(12) United States Patent
Gunday et al.

(10) Patent No.: US 10,576,231 B2
(45) Date of Patent: Mar. 3, 2020

(54) IMAGING STYLET FOR INTUBATION

(71) Applicants: Erhan H. Gunday, Great Neck, NY (US); Lawrence J. Gerrans, San Anselmo, CA (US); Alex Hsia, San Jose, CA (US)

(72) Inventors: Erhan H. Gunday, Great Neck, NY (US); Lawrence J. Gerrans, San Anselmo, CA (US); Alex Hsia, San Jose, CA (US)

(73) Assignee: Sanovas Intellectual Property, LLC, Reno, NV (US)

(*) Notice: Subject to any disclaimer, the term of this patent is extended or adjusted under 35 U.S.C. 154(b) by 0 days.

(21) Appl. No.: 15/604,905

(22) Filed: May 25, 2017

(65) Prior Publication Data

US 2017/0259020 A1 Sep. 14, 2017

Related U.S. Application Data

(63) Continuation of application No. 13/838,182, filed on Mar. 15, 2013, now Pat. No. 9,662,466.

(51) Int. Cl.
*A61B 1/00* (2006.01)
*A61M 16/04* (2006.01)
(Continued)

(52) U.S. Cl.
CPC ..... *A61M 16/0488* (2013.01); *A61B 1/00016* (2013.01); *A61B 1/00071* (2013.01); *A61B 1/00135* (2013.01); *A61B 1/00151* (2013.01); *A61B 1/00183* (2013.01); *A61B 1/05* (2013.01); *A61B 1/267* (2013.01); *A61M 16/0443* (2014.02); *A61B 1/0607* (2013.01); *A61M 16/0418* (2014.02); *A61M 2205/3375* (2013.01); *A61M 2205/502* (2013.01); *A61M 2205/505* (2013.01); *A61M 2205/80* (2013.01); *A61M 2205/8206* (2013.01); *A61M 2205/8243* (2013.01)

(58) Field of Classification Search
CPC ... A61B 1/00082; A61B 1/0057; A61B 1/267; A61B 1/2673; A61B 1/2766; A61B 1/273; A61B 1/2733; A61B 1/2736; A61B 1/3676; A61B 1/00098; A61B 1/00036
See application file for complete search history.

(56) References Cited

U.S. PATENT DOCUMENTS 3,081,767 A * 3/1963 Hett .................... A61B 1/00098
385/118
3,314,431 A 4/1967 Smith, Jr.
(Continued)

*Primary Examiner* — Timothy J Neal
(74) *Attorney, Agent, or Firm* — Forge IP, PLLC

(57) ABSTRACT

An imaging stylet is provided, including a deformable outer housing having a proximal end and a distal end with a longitudinal axis, and an opening provided at the distal end, an imaging device disposed at the distal end of the outer housing, a deformable support member disposed in the outer housing, and an actuator disposed in the outer housing and coupled to the imaging device. The imaging device is movable by the actuator from an inactivated position, in which the imaging device is substantially aligned with the longitudinal axis of the distal end, to an activated position, in which the imaging device extends out of the opening at an angle relative to the longitudinal axis of the distal end.

30 Claims, 11 Drawing Sheets

(51) Int. Cl.
  *A61B 1/05* (2006.01)
  *A61B 1/267* (2006.01)
  *A61B 1/06* (2006.01)

(56) References Cited

U.S. PATENT DOCUMENTS

| | | |
|---|---|---|
| 3,996,939 A | 12/1976 | Sheridan et al. |
| 4,742,819 A | 5/1988 | George |
| 5,329,940 A | 7/1994 | Adair |
| 5,803,898 A | 9/1998 | Bashour |
| 5,842,973 A * | 12/1998 | Bullard ............. A61M 16/0488 600/194 |
| 5,873,842 A | 2/1999 | Brennen et al. |
| 5,910,105 A | 6/1999 | Swain et al. |
| 6,322,498 B1 | 11/2001 | Gravenstein et al. |
| 6,929,600 B2 | 8/2005 | Hill |
| 7,052,456 B2 | 5/2006 | Simon |
| 7,070,559 B2 | 7/2006 | Adams et al. |
| RE39,508 E | 3/2007 | Parker |
| 2002/0099267 A1 | 7/2002 | Wendlandt et al. |
| 2003/0032863 A1 | 2/2003 | Kazakevich |
| 2004/0215061 A1 | 10/2004 | Kimmel et al. |
| 2004/0220451 A1 | 11/2004 | Gravenstein et al. |
| 2005/0054898 A1 | 3/2005 | Moriyama |
| 2006/0149129 A1 | 7/2006 | Watts et al. |
| 2007/0049794 A1 | 3/2007 | Glassenberg et al. |
| 2007/0074720 A1 | 4/2007 | Schwartz et al. |
| 2007/0129603 A1 | 6/2007 | Hirsh |
| 2007/0225740 A1 | 9/2007 | Suddaby |
| 2008/0017195 A1 | 1/2008 | Yoshida |
| 2008/0236575 A1 | 10/2008 | Chuda |
| 2008/0262523 A1 | 10/2008 | Makower et al. |
| 2009/0281500 A1 | 11/2009 | Acosta et al. |
| 2009/0322867 A1 | 12/2009 | Carrey et al. |
| 2010/0094088 A1 | 4/2010 | Ohline et al. |
| 2010/0145146 A1 | 6/2010 | Melder |
| 2010/0191050 A1 | 7/2010 | Zwolinski |
| 2010/0249513 A1 | 9/2010 | Tydlaska |
| 2011/0160537 A1 | 6/2011 | Chen |
| 2011/0207999 A1 | 8/2011 | Torisawa et al. |
| 2011/0306832 A1 | 12/2011 | Bassan et al. |
| 2012/0022326 A1 | 1/2012 | Jaime |
| 2012/0078055 A1 | 3/2012 | Berci et al. |
| 2012/0238805 A1 | 9/2012 | Iwasaka et al. |

* cited by examiner

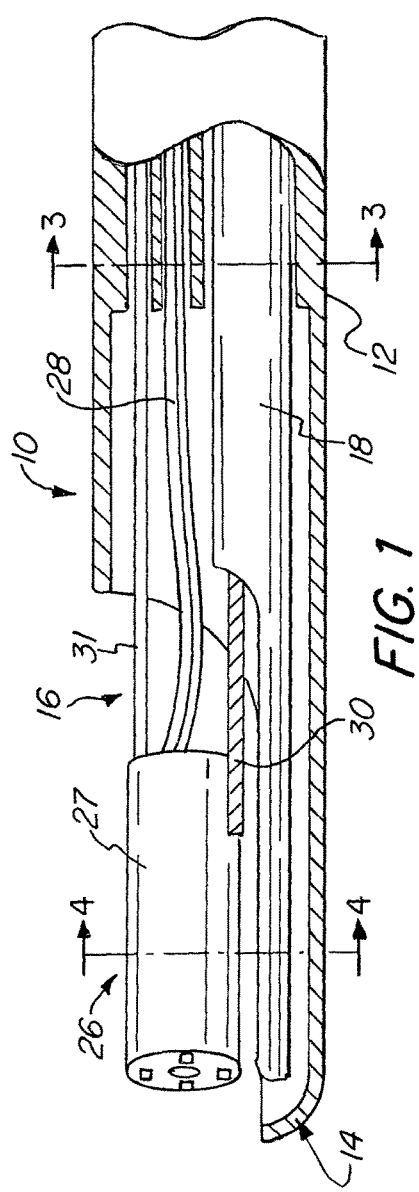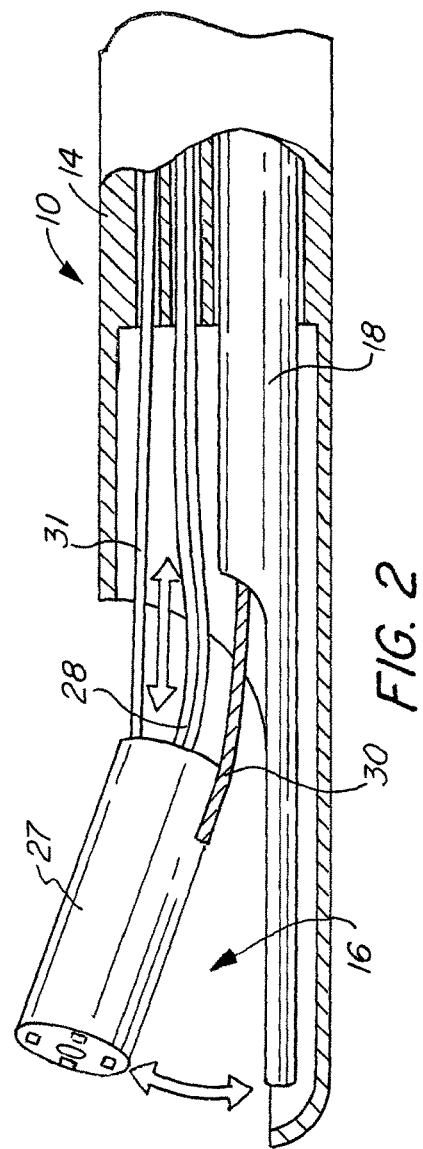

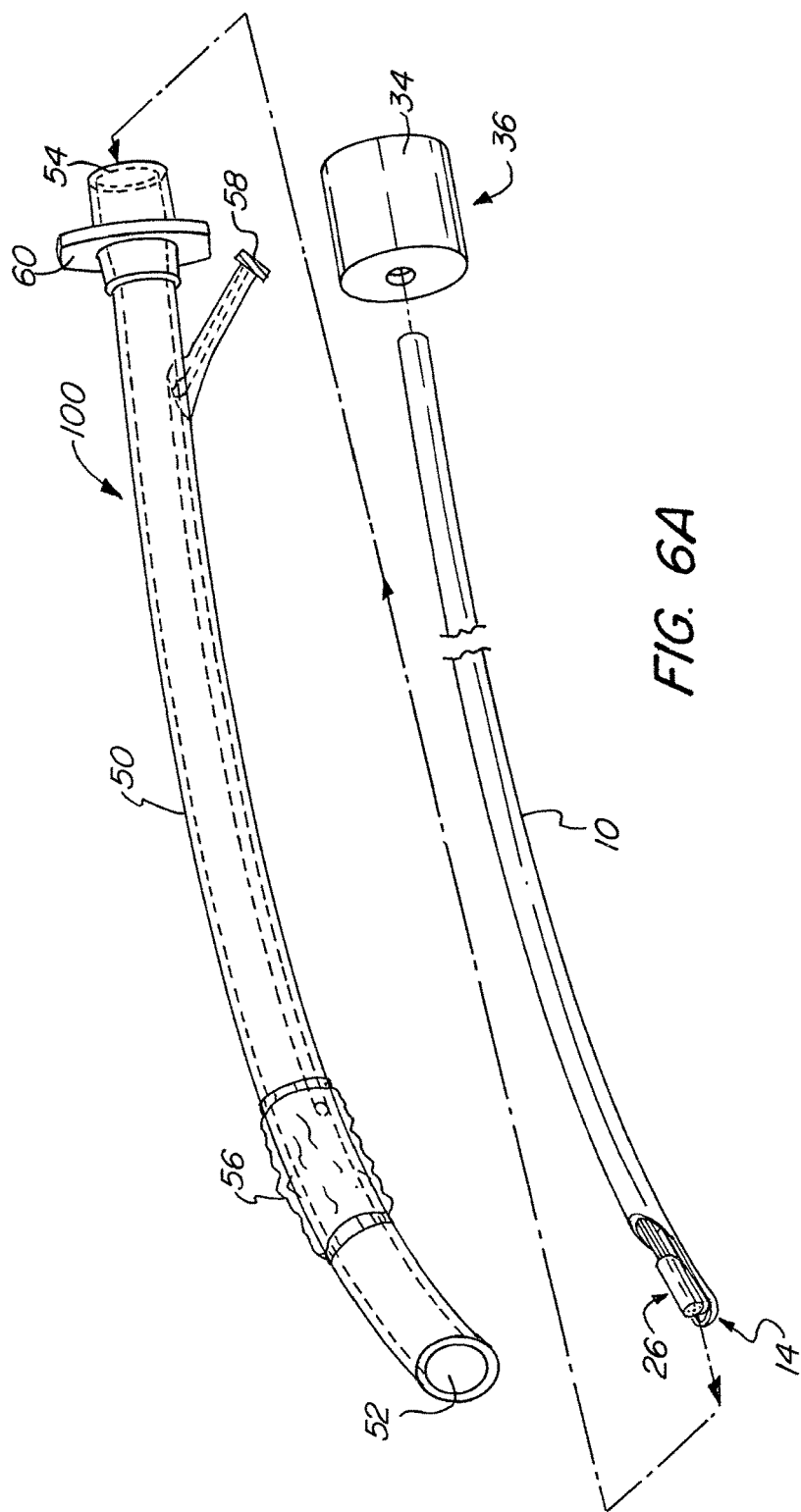

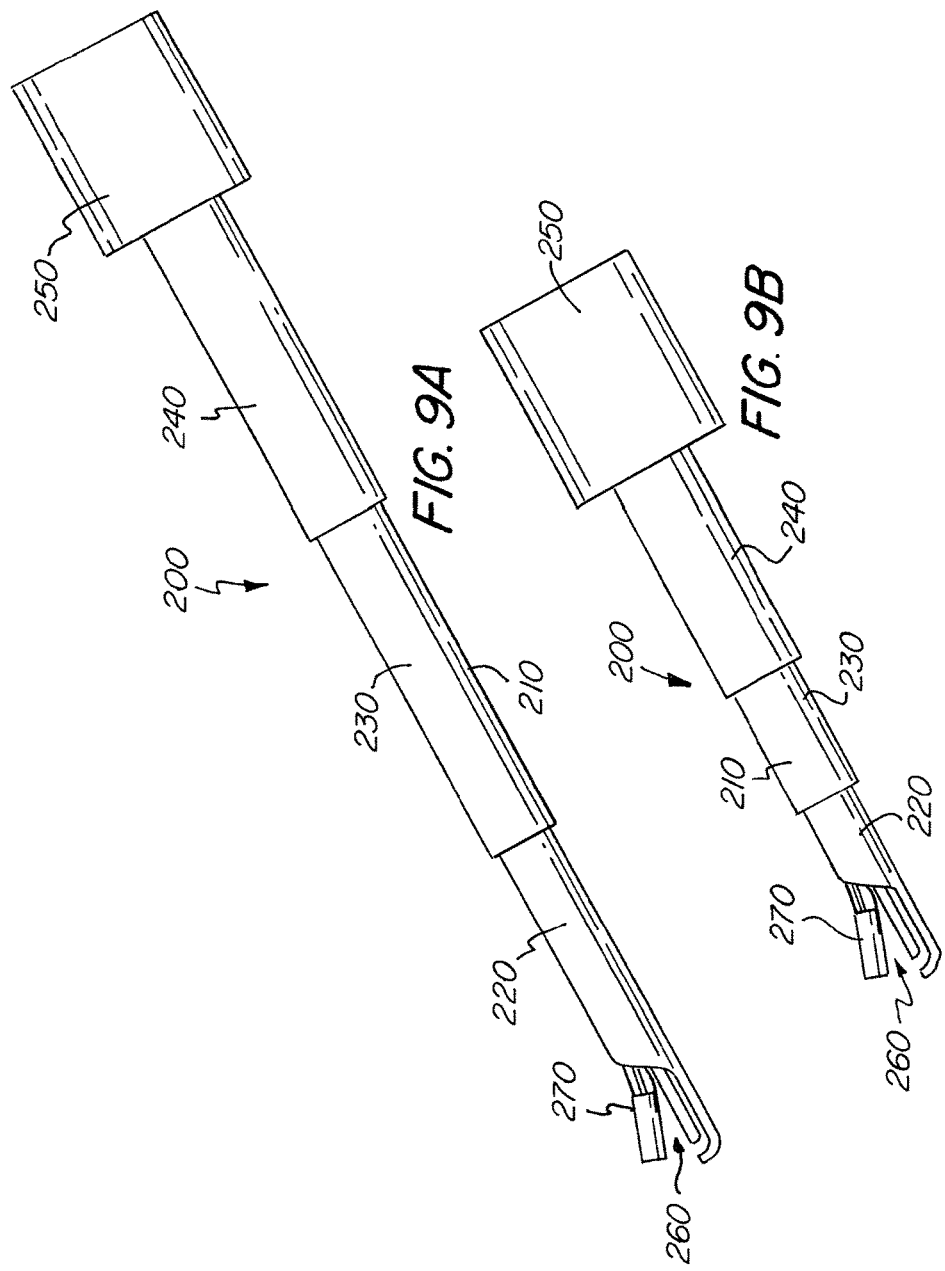

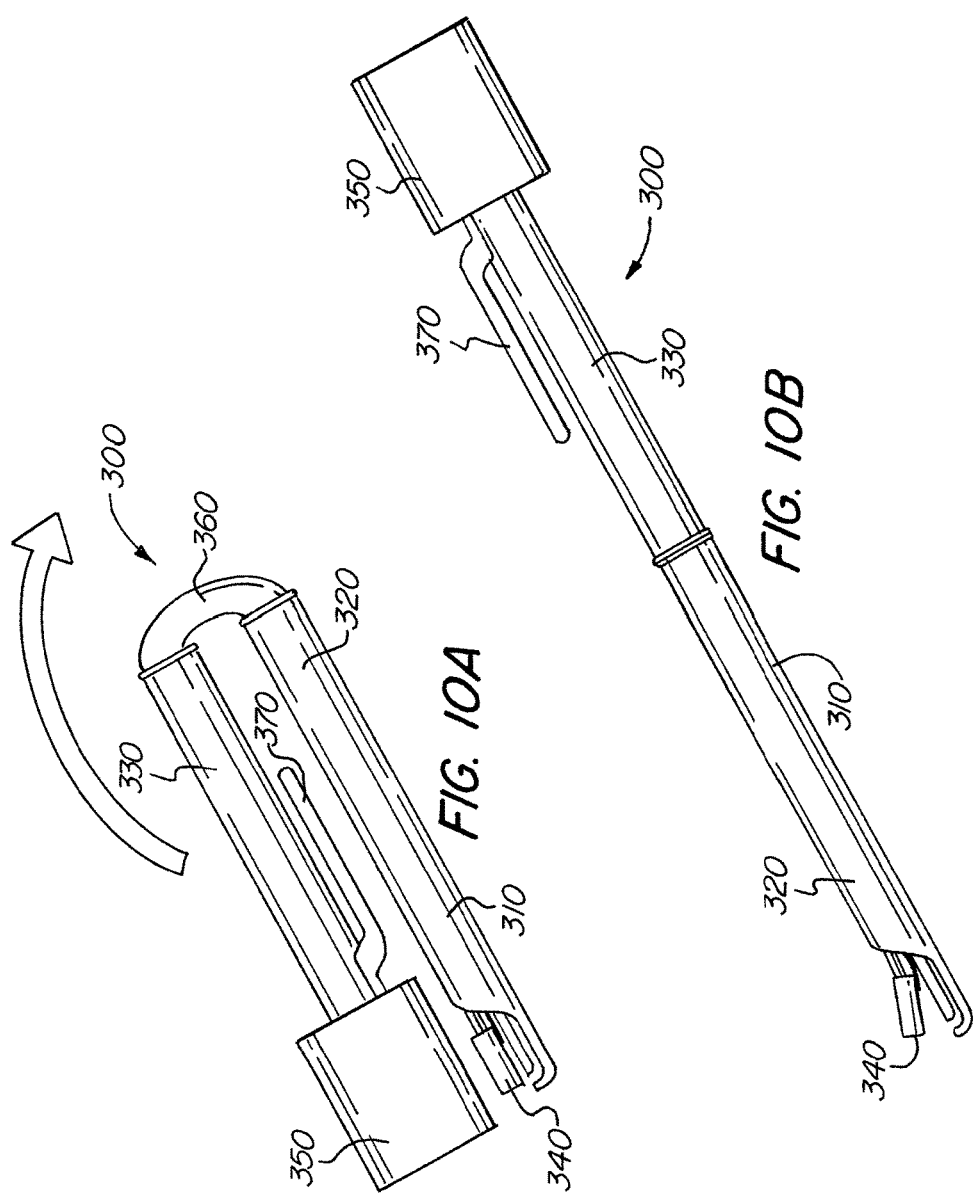

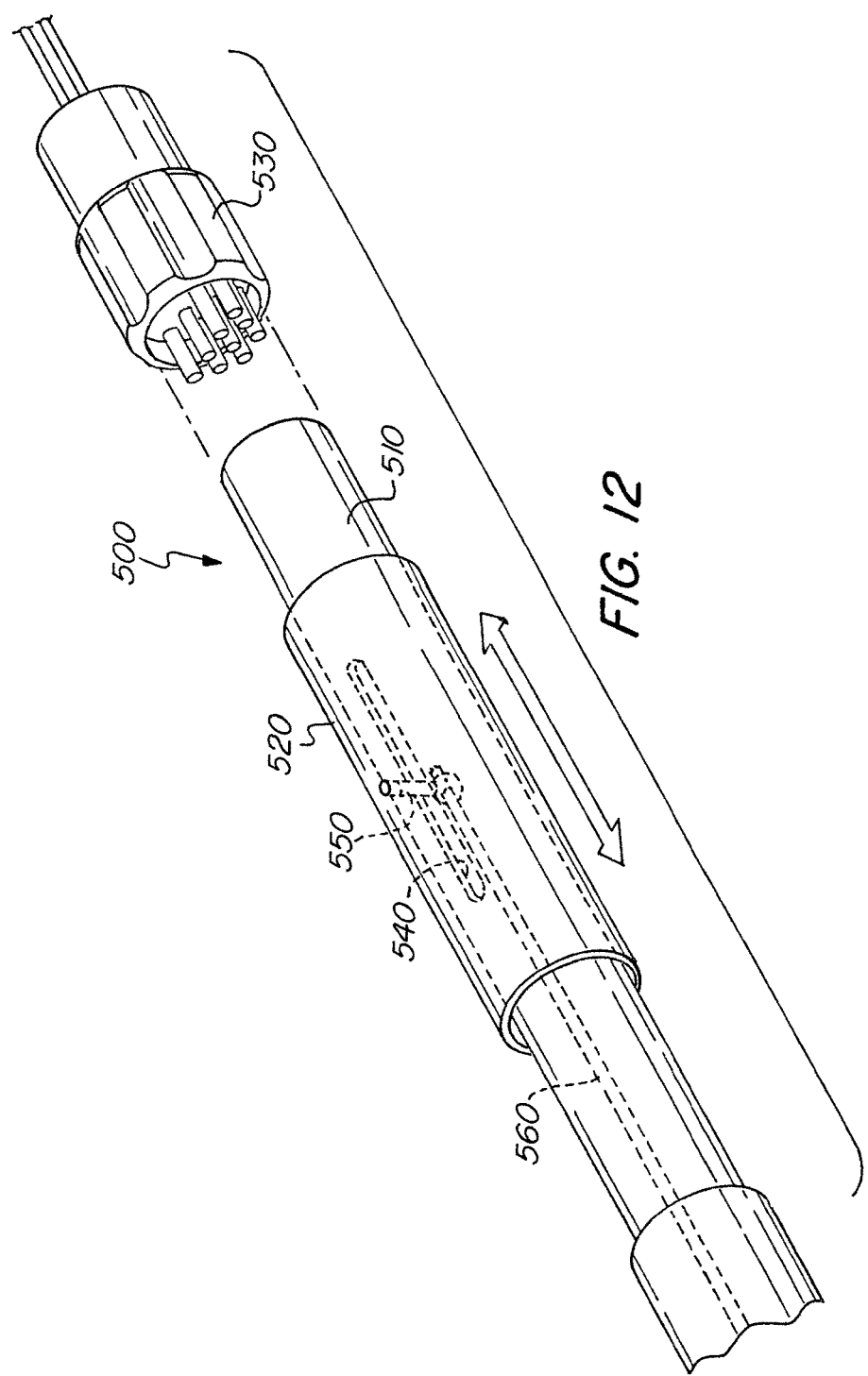

IMAGING STYLET FOR INTUBATION

FIELD OF THE INVENTION

The invention relates to a medical intubation device, and more specifically, to an imaging stylet having an imaging device that may be directed by a user to allow for enhanced visualization of surrounding tissue during the intubation procedure.

BACKGROUND OF THE INVENTION

In critically injured, ill or anesthetized patients, it is often necessary to insert an endotracheal tube into a person's airway to facilitate ventilation of the lungs and to prevent the possibility of asphyxiation or airway obstruction. The most common routes of inserting the endotracheal tube are oral, in which the tube is passed through the mouth and larynx into the trachea, and nasal, wherein the tube is passed through the nose and larynx into the trachea.

The insertion of the endotracheal tube often involves serious risks, such as damage to the vocal cords and a prolonged intubation procedure in which the patients breathing is stopped, but oxygen is not yet delivered to the patient as the tube has not yet been inserted. It is estimated that about one third of deaths occurring during a surgical procedure while under anesthesia for morbidly obese patients are associated with the intubation process. Some of the difficulties that persons performing endotracheal intubation encounter include the restriction of view as the tube is inserted, variations in the anatomy of the patients, an uncomfortable and unnatural position of the person performing the procedure while holding the instrument, and the necessity for rapid intubation.

With the advent of various video devices and cameras, instrumentation has been improved to the extent that it can enable viewing of the cords and larynx on a video screen thereby facilitating the intubation of the patient in a relatively quick and safe manner.

For example, US 2012/0022326 to Jaime describes an intubating stylet having an outer shaft, an inner shaft disposed within the outer shaft, and a hand grip housing positioned at the proximal end of the outer housing. A distal tip of the inner and outer shafts may be manipulated via a gear assembly. The stylet may further include optional video and light assembly positioned in the inner shaft.

US 2004/0215061 to Kimmel et al. describes a visualization stylet for endotracheal intubation including a flexible tube-shaped body defining a lumen therethrough, and an image gathering device and a light-emitting device positioned at or near the distal tip of the body. The distal tip of the stylet may be controlled by a user to allow visualization of internal structures.

U.S. Pat. No. 5,842,973 to Bullard describes a nasal intubation apparatus having a rigid curved body corresponding to the internal anatomy of a patient's airway passage. The body includes optical viewing and illumination channels disposed therein. The distal tip of the body is pivotable in a single direction to about 45 degree deflection via a thumb control provided at the proximal end of the body.

However, these known devices still suffer from a number of disadvantages and drawbacks. For example, one major problem with current systems is the limited field of view, requiring more time for the user to intubate the patient. Typically, the imaging device is positioned at a distal tip of the device body which only provides a limited view of the surrounding tissue, even if the distal tip is capable of being angled to a certain degree.

Additionally, with the current systems, the entire distal portion of the device has to be articulated to provide for better visualization. Such articulation is usually difficult to achieve due to a larger diameter and resilient nature of the materials used, and typically requires complex and bulky actuation mechanisms.

Furthermore, known systems typically utilize rigid bodies that are pre-shaped to have a certain curvature generally corresponding to the curvature of a person's airway passage anatomy. However, different types of patients often have different anatomies—for example, for a baby, the stylet body will typically have to be curved differently that for an adult patient. Therefore, a different type of stylet with different body curvature has to be used for different types of patients because the stylet cannot be easily adjusted to fit the anatomy of a particular patient.

Yet further drawbacks and disadvantages of these known optical and illuminating stylets relate to the substantial departure these devices have made from traditional stylets. The structure and design of traditional stylets allow for the endotracheal tube to be easily slipped over the stylet, once positioned, and further allow for the stylet to be easily removed from within the cannulation of the endotracheal tube once it has been positioned. The current systems require significant time to set up and to pre-assemble to the endotracheal tube. In emergent situations this delay could be hazardous, if not deadly.

What is desired, therefore, is an improved system and method for intubating a patient that address the disadvantages and shortcoming of the prior art systems described above.

SUMMARY OF THE INVENTION

It is therefore desired to provide an improved imaging stylet that provides the user with a greater field of view and that allows the user to observe virtually all of the larynx and the trachea as the intubation system is advanced.

It is further desired to provide an improved imaging stylet that facilitates a quicker intubation and reduces the probably of injuring the patient.

It is also desired to provide an improved imaging stylet that provides enhanced user control during the intubation process.

It is yet further desired to provide an improved imaging stylet that can be quickly and easily assembled with other components of an intubation system to facilitate emergent intubation of a patient.

In order to achieve at least the above-mentioned objects of the present invention, an imaging stylet is provided, including a deformable outer housing having a proximal end and a distal end with a longitudinal axis, and an opening provided at the distal end, an imaging device disposed at the distal end of the outer housing, a deformable support member disposed in the outer housing, and an actuator disposed in the outer housing and coupled to the imaging device, wherein the imaging device is movable by the actuator from an inactivated position, in which the imaging device is substantially aligned with the longitudinal axis of the distal end, to an activated position, in which the imaging device extends out of the opening at an angle relative to the longitudinal axis of the distal end.

In some embodiments, the angle at which the imaging device extends from the outer shaft is in the range of from about five degrees to about forty degrees.

In certain embodiments, the imaging stylet further includes a control device at the proximal end of the outer housing coupled to the actuator for moving the imaging device. In some of these embodiments, the control device is removably coupled to the proximal end of the outer housing.

In certain advantageous embodiments, the control device comprises a sleeve disposed over the proximal end of the outer housing and movable relative to the outer housing, and the actuator comprises a wire connected to the sleeve, such that movement of the sleeve relative to the outer housing causes the actuator to move the imaging device. In some of these embodiments, the proximal end of the outer housing has a wall with an aperture therein, and the actuator is connected to the sleeve through the aperture. In some cases, the aperture is a slit having a first end and a second end, the actuator is connected to the sleeve by a stop member extending through the slit, and the stop member is movable between the first end of the slit and the second end of the slit to move the imaging device between the inactivated and activated positions.

In some cases, the outer housing is an extruded cylinder having at least a support lumen for receiving the deformable support member, an actuation lumen for receiving the actuator and an imaging lumen for receiving the imaging device.

In certain advantageous embodiments, the actuator is a nitinol or stainless steel wire.

In some embodiments, the imaging device is at least one of a CMOS device and a CCD device.

In certain embodiments, the imaging device further includes at least one illumination device generating light for illuminating surrounding tissue. In some of these embodiments, the at least one illumination device is at least one light emitting diode.

In some advantageous embodiments, the imaging stylet further includes a processor coupled to and receiving image data from the imaging device. In certain of these embodiments, a display is further coupled to the processor for displaying image data received from the imaging device. In some advantageous embodiments, the image data generated by the imaging device is wirelessly transmitted to the processor. In other advantageous embodiments, the image data generated by the imaging device is transmitted to the processor via a cable connection.

In certain embodiments, the imaging stylet further includes a power source providing electrical power to the imaging stylet.

In some embodiments, the imaging stylet also includes a storage coupled to the imaging stylet for storing image data generated by the imaging device.

In certain advantageous embodiments, the outer housing includes at least two telescoping sections, wherein the outer housing is extended from an inactivated position, in which the at least two telescoping sections are disposed within each other, to an activated position, in which the at least two telescoping sections are extended out of each other such that a maximum length of the outer housing is achieved. In some of these embodiments, moving the outer housing from the inactivated position to the activated position activates a power source and initiates transmission of image data from the imaging device.

In certain embodiments, the outer housing includes at least two foldable sections, and wherein the outer housing is movable from an inactivated position, in which the at least two foldable sections are folded onto each other, to an activated position, in which the at least two foldable sections are unfolded such that a maximum length of the outer housing is achieved. In some of these embodiments, moving the outer housing from the inactivated position to the activated position activates a power source and initiates transmission of image data from the imaging device.

In some embodiments, the outer housing further includes a coupling device for securing the imaging stylet to an object.

In certain embodiments, the deformable support member comprises a semi-rigid material.

A medical intubation device is also provided, including an outer tube having a proximal end opening and a distal end opening, an inflatable balloon positioned adjacent the distal end opening, and an imaging stylet movably disposed in the outer tube through the proximal end opening and extendable out of the distal end opening. The imaging stylet includes a deformable outer housing having a proximal end and a distal end with a longitudinal axis, and an opening provided at the distal end, an imaging device disposed at the distal end of the outer housing, a deformable support member disposed in the outer housing, and an actuator disposed in the outer housing and coupled to the imaging device. The imaging device is movable via the actuator from an inactivated position, in which the imaging device is substantially aligned with the longitudinal axis of the distal end, to an activated position, in which the imaging device extends out of the opening at an angle relative to the longitudinal axis of the distal end.

In some embodiments, the medical intubation device also includes a fluid source for inflating the inflatable balloon to anchor the intubation device in a patient's airway passage.

A method of intubating a patient with a medical intubation device is further provided, including the steps of inserting an imaging stylet into a lumen of an outer tube, wherein the imaging stylet includes a deformable outer housing having a proximal end and a distal end with a longitudinal axis, and an opening provided at the distal end, an imaging device disposed at the distal end of the outer housing, a deformable support member disposed in the outer housing, and an actuator disposed in the outer housing and coupled to the imaging device. The method also includes inserting the outer tube with the imaging stylet into a patient's airway passage such that the imaging stylet extends out of a distal end of the outer tube, and moving the imaging device from an inactivated position, in which the imaging device is substantially aligned with the longitudinal axis of the distal end, to an activated position, in which the imaging device extends out of the opening at an angle relative to the longitudinal axis of the distal end, to visualize surrounding tissue in the airway passage.

In some embodiments, the method further includes the step of transmitting image data from the imaging device to a display coupled to the imaging stylet for display to a user.

In certain embodiments, the imaging stylet further includes a control device positioned at the proximal end of the stylet, and the method further includes the step of rotationally moving the imaging device via the control device.

In some cases, the outer tube has an inflatable balloon positioned adjacent the distal end of the tube, and the method further includes the step of inflating the balloon by supplying fluid thereto to anchor the outer tube within the airway passage.

In certain advantageous embodiments, the imaging stylet further includes at least one illumination device, and the method further includes the step of illuminating surrounding tissue via the at least one illumination device.

Other objects of the invention and its particular features and advantages will become more apparent from consideration of the following drawings and accompanying detailed description.

BRIEF DESCRIPTION OF THE DRAWINGS

FIG. 1 is a partially cross-sectional view of an imaging stylet in accordance with the present invention.

FIG. 2 is a partially cross-sectional view of the imaging stylet of FIG. 1, showing actuation of the imaging device.

FIGS. 6A-B are exploded views of a medical intubation systems incorporating the imaging stylet of FIG. 1.

FIGS. 9A and 9B are perspective views of the imaging stylet of FIG. 1 with a telescoping capability.

FIGS. 10A and 10B are perspective views of the imaging stylet of FIG. 1 with a folding capability.

FIG. 12 is an enlarged exploded view of the proximal end of the imaging stylet of FIG. 1, showing another type of the control device.

DETAILED DESCRIPTION OF THE INVENTION

Figure 3:
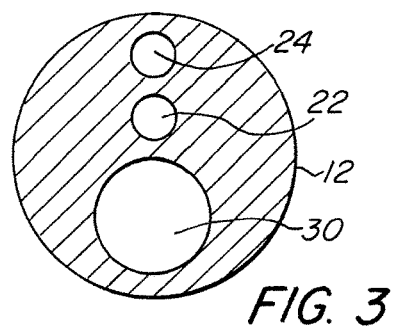
FIG. 3 is a cross-sectional view of the imaging stylet of FIG. 1 along line "3-3".

The basic components of one embodiment of an imaging stylet in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

As shown in FIG. 1, an imaging stylet, generally indicated at reference character (10), includes an outer housing (12) having a distal end (14) and a proximal end (not shown), and an opening (16) provided at the distal end. The outer housing (12) is made of any suitable malleable material, such as polyether block amide material (Pebax®), which preferably has a low modulus of elasticity with minimized resistance to bending. The outer diameter of the outer housing (12) should usually be made as small as possible. Typically, the outer diameter is less than about 5 mm. Preferably, the outer diameter of the catheter body is less than 3 mm.

In one advantageous embodiment shown in FIG. 3, the outer housing (12) is an extruded cylindrical member having at least three inner lumens (20, 22, 24). The inner lumens accommodate various components of the imaging stylet (10), as described in more detail below. It is understood, however, that any other suitable structure/configuration of the outer housing (12) may be utilized in accordance with the present invention.

Figure 4:
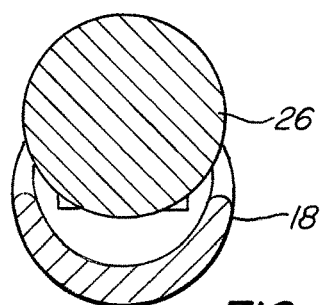
FIG. 4 is a cross-sectional view of a portion of the imaging stylet of FIG. 1 along line "4-4".

Referring back to FIG. 1, the imaging stylet (10) also includes a (18) disposed within the outer housing (12). In an advantageous embodiment, the support member (18) is disposed in a support lumen (20) of the outer housing (12). The support member is preferably a solid rod having a cup-shaped portion at its distal end, as shown in the cross-sectional view in FIG. 4. The support member is constructed with any suitable malleable semi-rigid material, such as aluminum, that is capable of being bent to a certain shape and also being capable of retaining that bent shape. Before use, the support member (18) is first bent to a certain angulation that corresponds to a shape of larynx and trachea of a particular patient being intubated. The support member (18) provides rigidity to the flexible outer housing (12) to facilitate the intubation process.

An imaging device (26) is further disposed in the outer housing (12), preferably via an imaging device lumen (22). The imaging device includes an imaging device head (27) positioned adjacent the opening (16) at the distal end of the outer housing (12). Any suitable type of imaging device may be used in accordance with the present invention. In one exemplary embodiment, the imaging device (26) is a camera provided with a fiber optic image bundle introduced through the imaging device lumen (22) of the outer housing (12) via a port provided at the proximal end to image the surrounding area. The fiber optic image bundle may be made of coherent imaging fibers at the core, and a lens provided at the distal end of the camera head (27). The camera may incorporate various types of object lenses at the distal tip for different fields of view (i.e. 50°, 130°, etc.) and various depths of field. At the proximal end of the fiber optic bundle, the coherent imaging fibers may be interfaced to any suitable type of digital imaging device, including, but not limited to, a CMOS device or a CCD.

Figure 5:
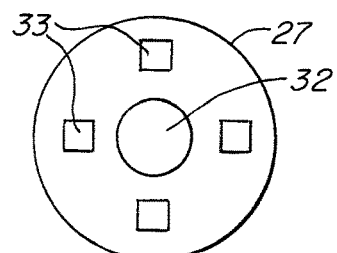
FIG. 5 is a distal end view of an imaging device of the imaging stylet of FIG. 1.

In some advantageous embodiments, the imaging device (26) further includes at least one illumination device for illuminating surrounding tissue during the intubation process. For example, as shown in FIG. 5, the imaging device head (27) includes four light emitting diodes (33) positioned around the camera lens (32). It should be noted, however, that other sources of illumination may also be employed. For example, in other embodiments, two separate bundles, one for illumination and the other for image can also be used. Similarly to the cohered fibers, the illumination fibers are interfaced to a light source. It should also be noted that the image sensor can be located at the distal end of the imaging device head (27), eliminating the need for a coherent imaging fiber bundle, thus increasing the image quality and reducing cost.

The imaging device head (27) is attached to a distal end of the support member (18) by a resilient member (30). The resilient member (30) is made with any type of suitable material that returns to its original form after being deformed. In one advantageous embodiment, the resilient member (30) is a leaf-spring.

The imaging device head (27) is further connected to an actuator (31) disposed in an actuation lumen (24) of the outer housing (12). In the exemplary embodiment shown in FIGS. 1 and 5, the actuator (31) is a push/pull wire, a distal end of which is connected to the imaging device head (27) and a proximal end of which is coupled to a control device provided at the proximal end of the outer housing (12), as described in more detail below. The guide wire is made out of any suitable material. In one advantageous embodiment, the guide wire is made with nitinol or stainless steel.

In its inactivated position, the imaging device head (27) is aligned with the longitudinal axis of the distal end (14) of the outer housing (12) such that it lays flat on the cup-shaped distal portion of the support member (18). When the push/ pull wire (31) is pulled by the user via the control device, the imaging device head (27) is brought from its inactivated position to an activated position, wherein it extends out of the opening (16) in the outer housing (12) at a certain angle relative to the longitudinal axis of the housing, as shown in FIG. 2. The angle at which the imaging device (26) extends out of the outer housing (12) may be adjusted as desired to facilitate viewing of the patient's larynx and trachea anatomy during the intubation process. In some advantageous embodiments, the angle is in the range of from about five degrees to about forty degrees. It should be noted that any other type of actuation device may also be used to actuate the imaging device (26) in accordance with the present invention.

It is noted that, in certain advantageous embodiments, the outer housing (12) includes imaging markers, such as radio opaque rings, located throughout the length of, or at or near, the distal end (14). Such markers can be selected and appropriately positioned in order to reflect the relevant waves of various imaging modalities (e.g., x-ray) in order to allow the use of such modalities to assist with the precise positioning of the imaging stylet (10) within the patient's airway passage.

As shown in FIG. 6A, the imaging stylet (10) further includes a control device (34) provided at the proximal end (36) of the outer housing (12) for manipulation of the imaging device (26) by the user. Any suitable type of control device may be used in accordance with the present invention. In one advantageous embodiment, the control device (34) may be in the form of a handle with a pistol-type grip and a trigger-type lever having a closed loop into which a user may insert a finger. In other advantageous embodiment, the control device (24) may be a hand piece having one or more control mechanisms, such as joysticks and/or buttons, to actuate the imaging device. In some embodiments, the control device (34) and/or handle is removable in order to permit removal or insertion of an outer tube (50) over the stylet (10), as further described below.

In certain advantageous embodiments, the imaging stylet (10) further includes a storage device (not shown), which is provided to store, for example, the image data captured by the imaging device (26). The storage device may comprise virtually any type of storage device and may be internal or external to the control device (34). For example, suitable storage devices include a magnetic, high density hard drive, a writable medium including a CD/DVD, or a card inserted into the screen casing including, for example, a removable drive, such as a thumb drive, volatile or non-volatile memory, etc. It is further contemplated that the storage device may have saved thereon configuration data for configuration of the control device (34) so that control device may properly process the received image data and control the imaging device (26).

Figure 7:
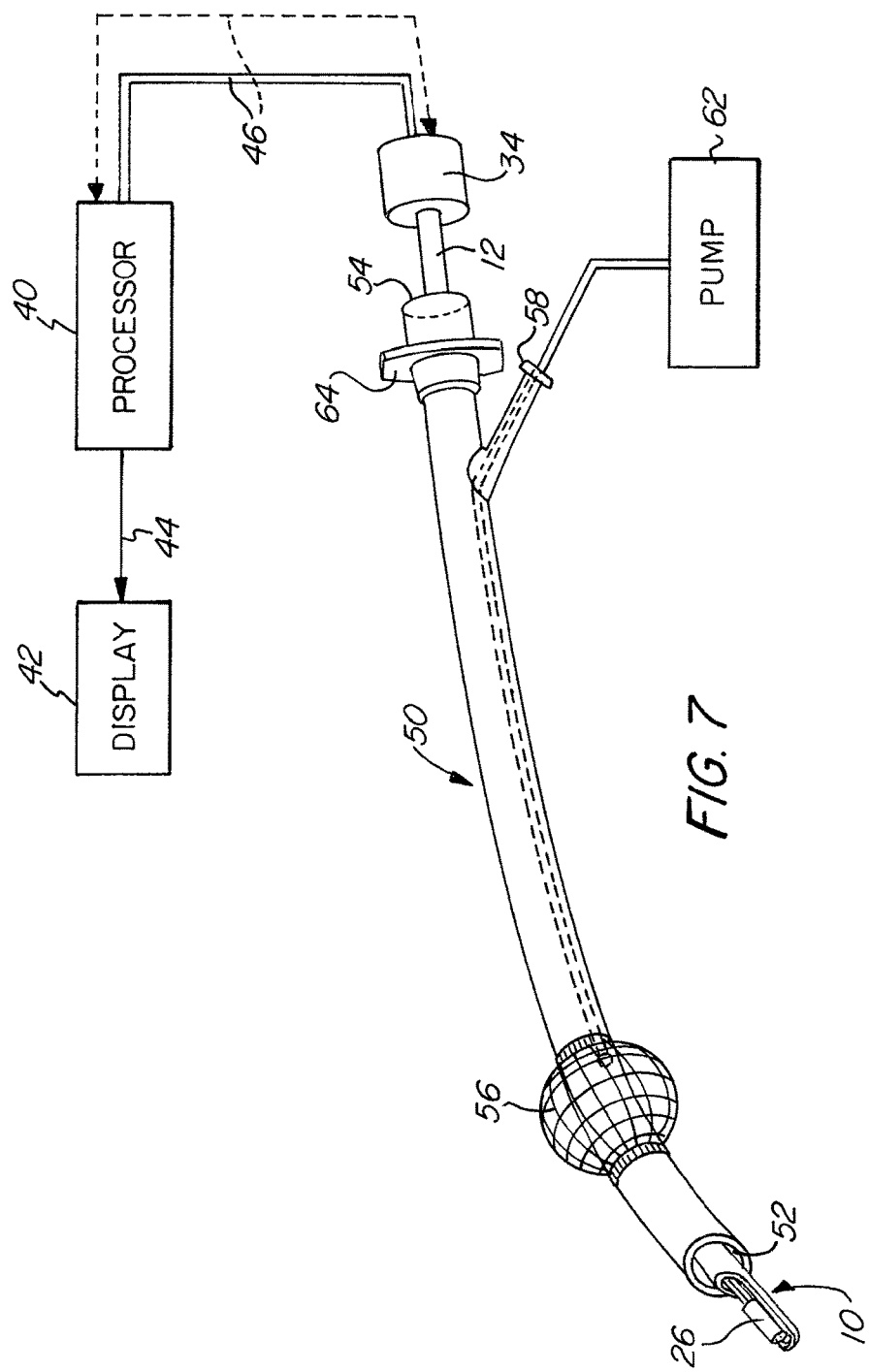
FIG. 7 is a schematic view of a medical intubation system incorporating the imaging stylet of FIG. 1.

As shown in FIG. 7, the imaging stylet (10) is coupled to a processor (40) via the control device (34) for receiving and processing image data captured by the imaging device. Any suitable type of a processor may be used. The imaging stylet (10) is connected to the processor (40) via a cable connection (46), which may comprise, for example, an optical channel and a data channel. Alternatively, it is understood that the imaging stylet (10) may be wirelessly coupled to the processor (40) via a network connection. It is contemplated that network connection may comprise, for example, an Internet connection.

The processor (40) may be coupled to a remote storage, which may comprise virtually any type of memory device, as described above. Additionally, virtually any type of digital data may be saved on remote storage, such as, but not limited to, configuration data, update information, image data, etc. The processor (40) is further connected to a display (42) via a cable or wireless connection (44), for displaying the processed image data to the user. The display (42) may be any suitable type of display, such as a computer monitor or a television screen.

It is noted, however, that in some embodiments, the image data generated by the imaging device (26) may also be processed by the control device (34) positioned on the imaging stylet (10). In such embodiments, the processed image data may then be transmitted from the control device (34) to the processor (40) via cable or wirelessly. The processor (40) may be used to further process the information and/or transmit the image data to the display (42).

It should further be noted that connection (46) coupling the imaging stylet (10) to the processor (40) is illustrated with a two-way arrow, which is provided to indicate two-way communication. For example, in addition to the imaging data captured by the imaging device (26), the imaging stylet (10) may transmit stylet information, such as, for example, identification/use/maintenance data, to the processor (40). The processor (40) may then use this information to automatically configure to function properly with the imaging stylet (10). Additionally, command and control data may be transmitted to the imaging stylet (10) from the processor (40), which may include commands for moving the imaging device head (27) or bending the stylet (10). In such embodiments, an input device, such as keyboard, mouse, track pad, microphone, etc., may be coupled to the processor (40) and used by a user to provide input commands for the imaging stylet (10). It is further contemplated that, rather than having a separate input device, the display (42) may be provided as a touch screen control device, which may be used to both display image data and provide for control/command inputs.

The imaging stylet (10) may include a power cable for providing electrical power to the electronics and illuminating device, or electrical power may be provided via battery power (such as a rechargeable battery) positioned on the stylet or removably connected to the stylet. Alternatively, it is contemplated that the imaging stylet (10) may be wirelessly powered via any known coupling devices.

As shown in FIG. 6A, the imaging stylet (10) may be used as a part of medical intubation system (100). The medical intubation system (100) further includes a hollow outer tube (50) having a proximal end opening (54) and a distal end opening (52). The outer tube is constructed of any suitable elastomeric material, such as, for example, the materials described above with respect to the outer housing (12). The outer diameter of the outer tube (50) varies depending on the particular type of patient that is being intubated, e.g. a child or an adult. The outer tube diameter is chosen such that it is smaller than the inner diameter of the patient's airway passage to ensure a safe and comfortable intubation process. An inner diameter of the outer tube (50) is sufficiently large to accommodate the imaging stylet (10) and also provide sufficient space for passage of air to and from the patient's lungs during intubation. The outer tube (50) includes a handle (60) or any other suitable structure for manipulation of the outer tube (50) within the patient's airway passage.

As shown in FIGS. 6 and 7, the imaging stylet (10) is inserted into the outer tube (34) via the proximal end opening (54) and the distal end of the imaging stylet (10) with the imaging device (26) is then extended out of the distal end opening (52) of the outer tube (34), such that the surrounding tissue can be visualized during the intubation process.

The outer tube preferably includes an inflatable balloon (56) positioned adjacent the distal end opening (52). The inflatable balloon may be made of latex, Yulex, polyethylene, nylon or other suitable material, and may come in a variety of sizes and diameters, depending, as described above, on a particular type of patient being intubated. In some advantageous embodiments, the balloon (56) has a wall with a textured outer surface that provides a gripping surface to facilitate anchoring the balloon (56) on the patient's airway passage. The textured outer surface of the balloon (56) may be formed by a fiber mesh affixed to the surface of the balloon during the molding process. The fiber mesh may be made of elastane, latex, lycra, polyurethane, nylon, nylon coated with other materials such as cotton, composite springs, or other appropriate material. In other embodiments, dimensional surface structures or inflatable sinuses that are encapsulated in the surface substrate of the balloon (56) may be used to produce the textured surface.

The outer tube (50) further includes a port (58) for connection to a fluid source (62), as shown in FIG. 7. Any suitable fluid source may be used, such as a hand-held pump or an electromagnetic pump to supply fluid to the inflatable balloon (56). It is also contemplated that, in alternative embodiments, the fluid source may be an integral part of the outer tube (50). The port (58) is provided with any suitable connector, such as a luer connector, for connection to the pump (62). The pump (62) supplies a fluid, such as a gas, liquid, or mixture thereof, to the inflatable balloon (56) to inflate it. The pump (62) may also include a variety of capabilities for balloon identification, proper inflation/deflation of the balloon, and feedback measurements, many details of which are described in U.S. Pat. No. 8,226,601 to Gunday et al. In certain advantageous embodiments, the pump (62) further includes a vacuum source to evacuate fluid from the balloon (56).

Figure 6B:
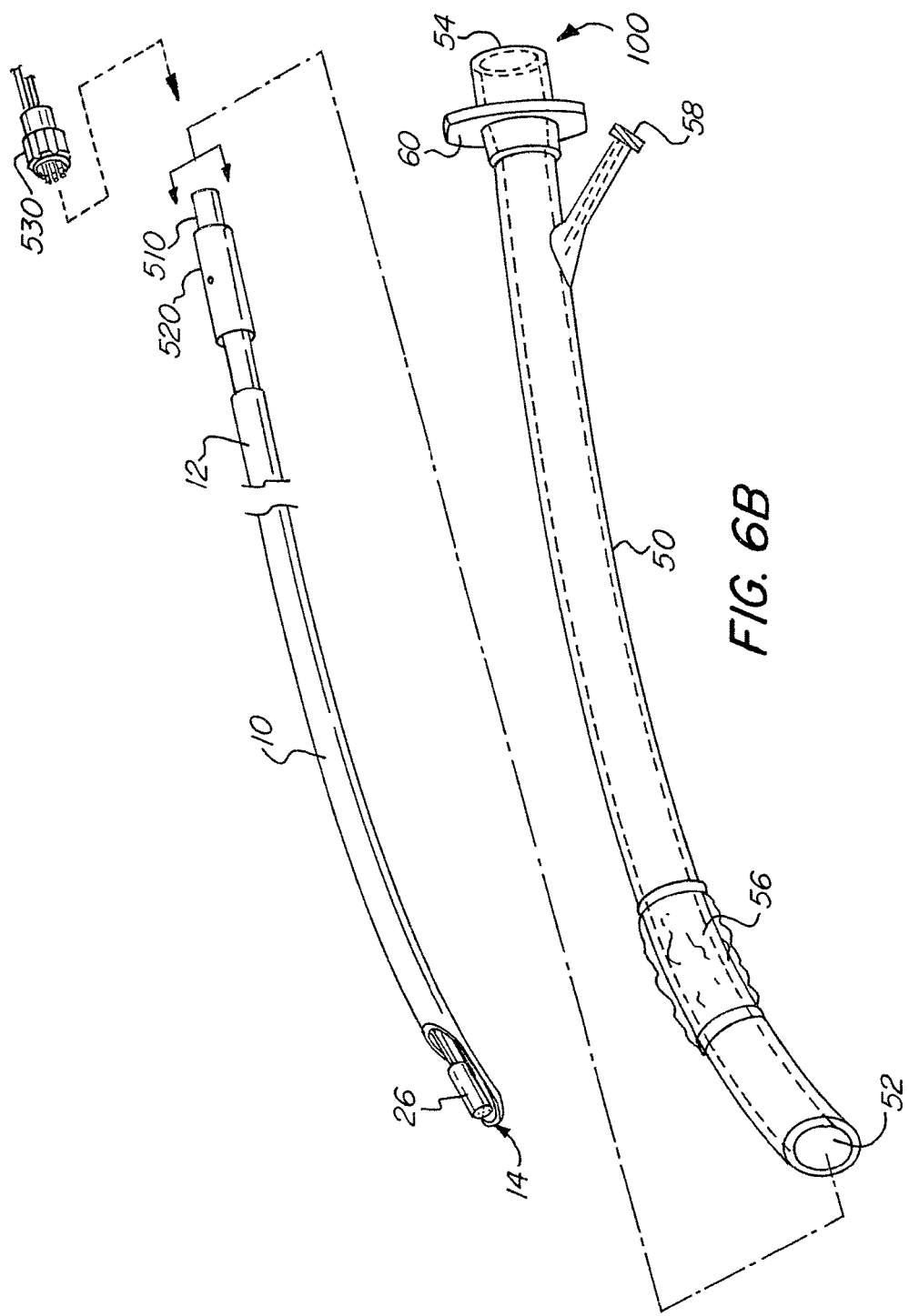

It is contemplated that, in certain advantageous embodiments, the imaging stylet (10) is first inserted into a person's airway passage with the guidance of the imaging device (26), as shown in FIG. 6B. Once the stylet (10) is positioned at a desired location in the person's trachea, the outer tube (50) is inserted onto the proximal end of the stylet (10), and is then slid over the stylet (10) to the target position in the trachea.

Figure 11:
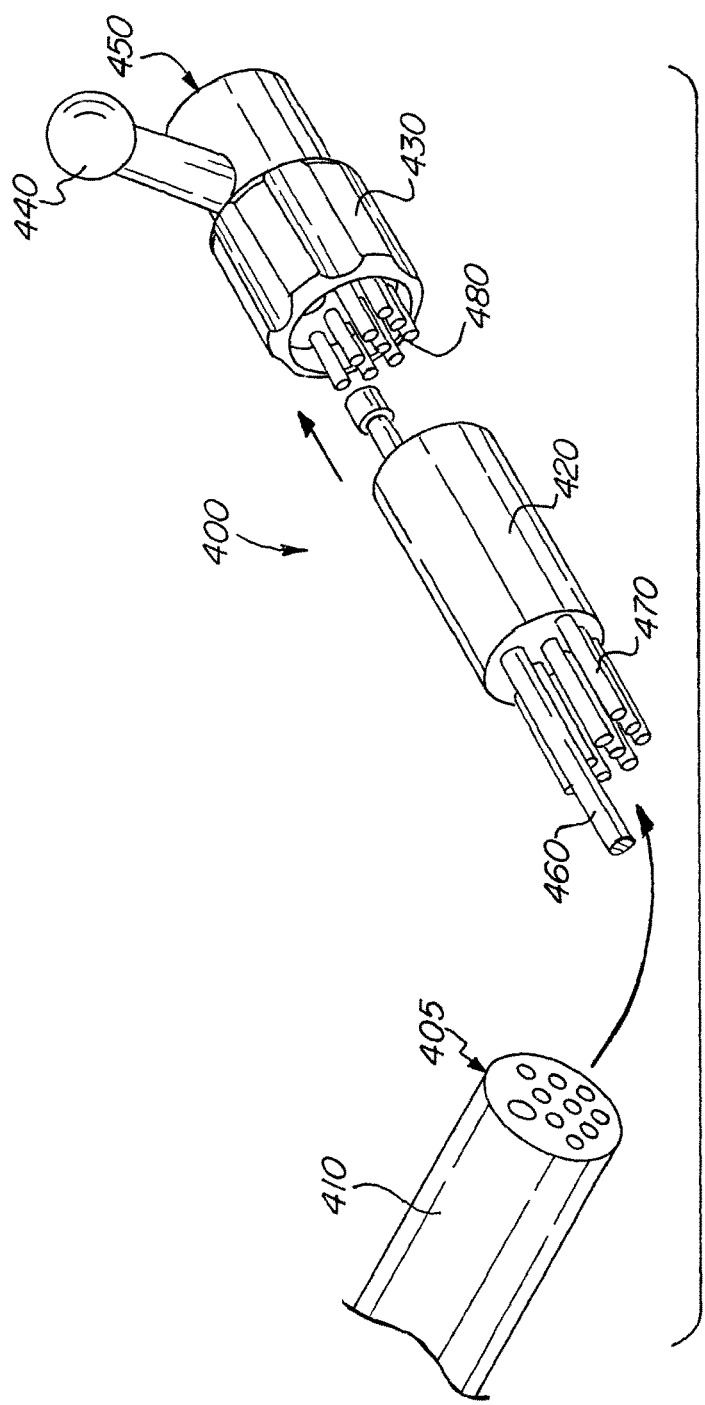
FIG. 11 is an enlarged exploded view of the proximal end of the imaging stylet of FIG. 1, showing the control device.

In these embodiments, it is advantageous to have a control device that has an outer diameter that is substantially the same as the outer diameter of the stylet housing, or at least smaller than the inner diameter of the outer tube (50), such that the outer tube (50) can be easily slid onto the stylet (10). FIG. 11 illustrates one such embodiment of the control device. As shown in this figure, the proximal end (405) of the imaging stylet (410) is removably coupled to a connector (420). The connector (420) provides a connection between the imaging stylet and the control device for the push/pull wire (460) and the imaging device cables/wires (470). It is understood that any suitable type of connector may be used. It is also understood that the connector (420) may be used with any type of control devices described herein.

A control device (430) is removably coupled to the proximal end of the connector (420). The control device includes an actuator (440), which is coupled to the push/pull wire (460) via the connector (420). The actuator (440) may be a lever, as shown in this figure, or any other suitable device. By moving the lever (440), the user can move the head of the imaging device between the inactivated and activated positions to visualize the internal anatomy of a patient's airway passage. The proximal end (450) of the control device (430) may include connections (not shown) to the external processor and/or display. The control device (430) is removable such that it can be temporarily disconnected in order to allow an outer intubation tube (50) to be slid on or off the stylet (10).

FIG. 12 illustrates another advantageous embodiment of the control device of the present invention. In this embodiment, the control device (520) comprises a slidable sleeve positioned over the proximal end of the imaging stylet housing (510). The housing has an elongated opening or slit (540) positioned adjacent the proximal end of the stylet such that it is covered by the slidable sleeve (520). The inner wall of the slidable sleeve (520) has a stop member (550) that extends from the sleeve (520) towards the center axis of the sleeve. The positioning of the stop member (550) corresponds to the positioning of the slit (540) of the stylet housing (510), such that the stop member slidably fits into the slit (540) when the sleeve (520) is positioned over the stylet housing (510). The push/pull actuator wire (560) extends out of the housing (510) through the slit (540) and is coupled to the slidable sleeve (520) via the stop member (550). The stop member (550) may comprise a rod, set screw, or any other suitable member.

When in use, the slidable sleeve (520) is positioned over the stylet housing (510), such that the stop member (550) corresponds to the aperture (540) in the housing, and the push/pull actuating wire (560) is connected to the stop member (550). Then, the user slides the sleeve (520) towards the proximal end of the stylet, thereby pulling the wire and moving the imaging device head at the distal end of the stylet into the activated angled position. The proximal motion of the sleeve (520) is limited by the stop member (550) once it reaches the proximal end of the slit (540).

When desired, the user can move the sleeve (520) in the distal direction of the stylet, thereby pushing the wire (560) and moving the imaging device head back into the inactivated position. The distal movement of the sleeve (520) is again limited by the stop member (550) once it comes into contact with the distal end of the slit (540). It is understood that the sleeve (520) may be moved in smaller increments to achieve the desired degree of angulation of the imaging device head.

The outer diameter of the slidable sleeve (520) shown in FIG. 12 is substantially smaller than the inner diameter of the outer intubation tube (50) such that the tube can be easily slid over the stylet (10) and inserted into the patient's airway passage. The proximal end of the stylet housing (510) has a removable connector (530) for providing a connection for cable/wire components of the imaging device, such that the connecting wires can be temporarily removed when an outer intubation tube (50) is slid on or off the stylet (10). Any suitable connector, such as described above in connection with FIG. 11, may be used.

Figure 8A:
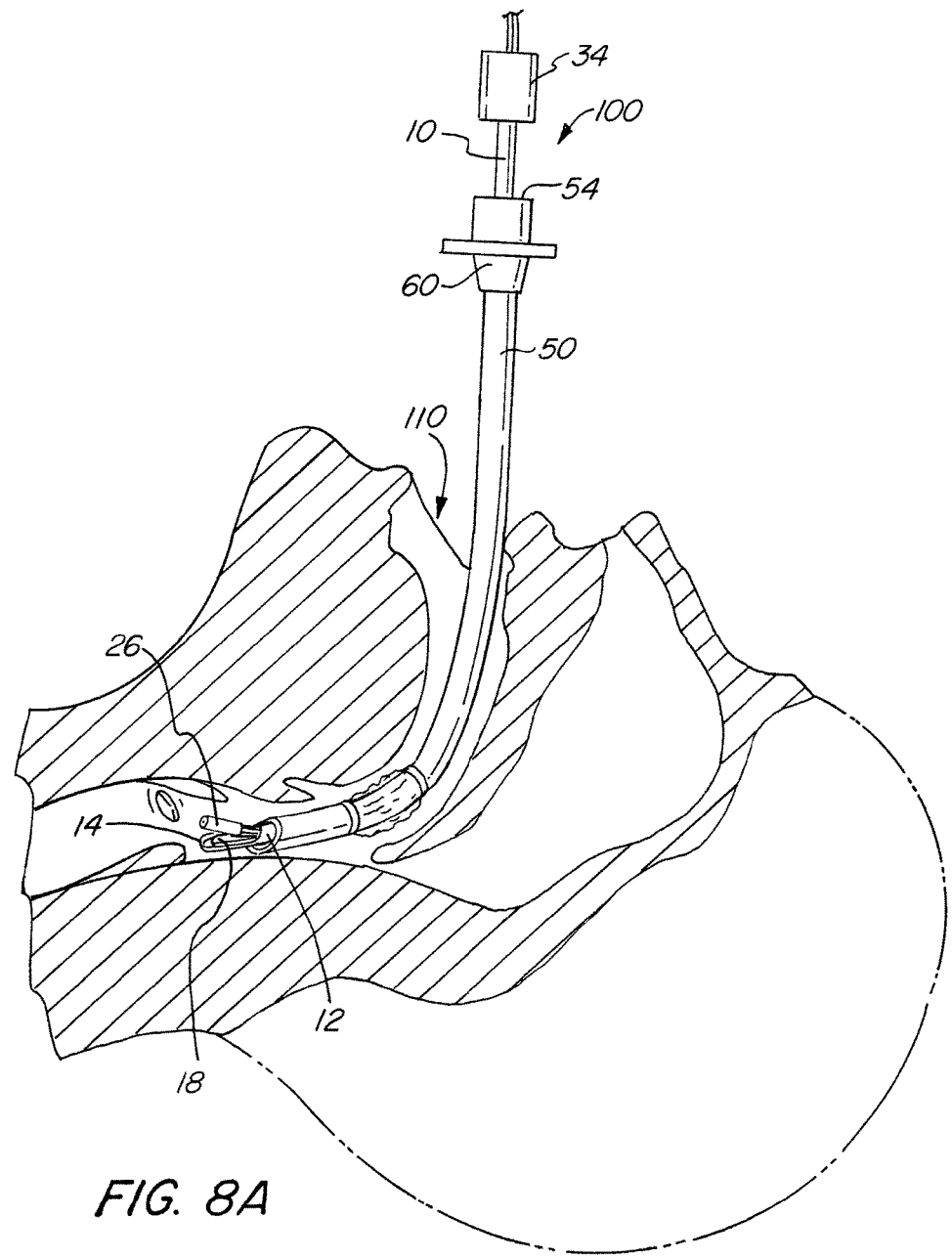
FIGS. 8A and 8B are perspective views of the medical intubation system of FIG. 7 being used in a patient's airway passage.
Figure 8B:
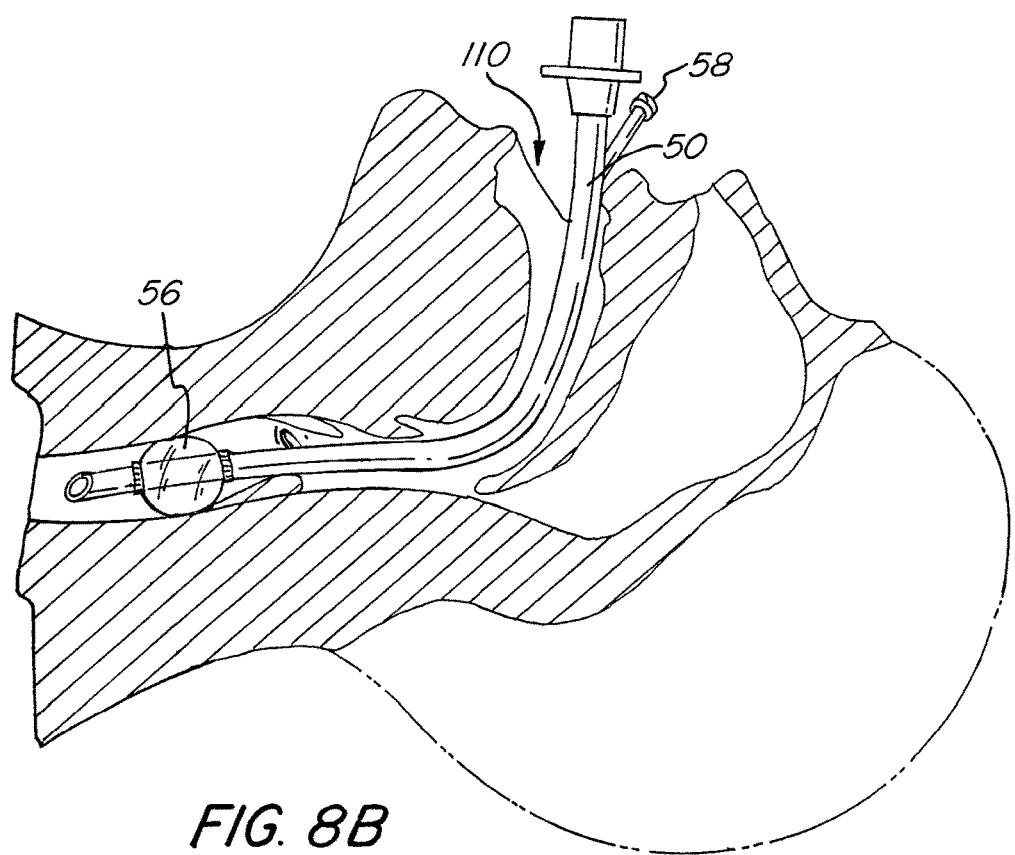

FIGS. 8A and 8B describe the operation of the intubation system (100) in a patient's airway passage. The support member (18) of the stylet (10) is bent to a shape that corresponds to the internal anatomy of a particular patient's airway passage and is inserted into the support lumen of the stylet. Then, as shown in FIG. 8A, the imaging stylet (10) in inserted into the outer tube (50) through the proximal end opening (54). It is also contemplated that the deformable support member (18) may be inserted into the support lumen of the stylet (10) first, and then the stylet (10) with the support member (18) disposed therein are bent to the desired shape.

This intubation assembly (100) is then inserted into a patient's mouth (110) and is guided through the patient's larynx into the trachea. The distal end (14) of the imaging stylet (10) is extended out of the distal end opening (52) of the outer tube (50), such that the anatomy of the larynx and trachea can be visualized by the physician during the intubation. In other advantageous embodiments, the stylet (10) may be inserted into the patient's airway passage first with the guidance of the imaging device (26). Once the stylet (10) is positioned at a desired location in the patient's trachea, the control device (34) may be removed from the stylet, and the outer tube (50) may be slid over the stylet and positioned within the patient's trachea.

The imaging device (26) is actuated by the control device (34) to bring the imaging device (26) into an angled position with respect to the longitudinal axis of the imaging stylet housing, as shown in FIG. 8A. The imaging device (26) may be angled as much as needed to visualize the anatomy of the larynx and trachea during the insertion to ensure that the patient's vocal cords or other internal structures are not damaged. If desired, the imaging stylet (10) is rotated via the control device (34) such that other sides of the patient's airway passage may be viewed as well. Thereby, the intubation system of the present invention allows for a complete 360 degree visualization of the airway passage anatomy.

Image data collected by the imaging device (26) is transmitted to the processor (40) either wirelessly or via a cable connection. The image data is processed and displayed to the user via the display (42). The illumination device provided on the distal end of the imaging stylet (10), as described above, provides light to illuminate the surrounding tissue to facilitate the visualization.

After the intubation assembly (100) is placed at a desired location within the person's airway passage, the balloon (56) provided at the distal end of the outer tube (50) is inflated by the fluid source via the port (58) to anchor the outer tube (50) within the airway passage, as illustrated in FIG. 8B. As described above, the balloon (56) may have a textured outer surface that assists in gripping to the airway passage walls. The imaging stylet (10) can then be removed from the outer tube (50) to provide for a better passage of air to and from the patient's lungs and/or provide a working channel for insertion of other necessary devices. When the intubation of the patient is no longer required, the balloon (56) is deflated via the port (58) and the outer tube (50) is removed from the patient's airway passage.

In some embodiments, it may also be desirable to remove the outer tube (50) from the person's airway passage while leaving the imaging stylet (10) in place in order to replace the tube (50) or to perform other medical procedures. In this case, the control device (34) may be disconnected from the proximal end of the imaging stylet outer housing (12) so that the outer tube (50) may be slid off the imaging stylet (10) and removed from the patient's mouth.

It should be noted that, although FIGS. 8A and 8B illustrate the use of the intubation system to incubate a patient through the mouth, the intubation system of the present invention may use be used for intubation procedures through a person's nasal cavity.

FIGS. 9A and 9B illustrate an embodiment of the imaging stylet in which the stylet has a telescoping capability. As shown in FIG. 9A, the outer housing (210) of the stylet includes three separate sections—a proximal section (240) coupled to the control device (250), a middle section (230), and a distal section (220) with an opening (260) through which the imaging device (270) is extended when in the activated position. The outer diameter of the distal section (220) is smaller than the inner diameter of the middle section (230), and the outer diameter of the middle section (230) is smaller than the inner diameter of the proximal section (240), such that the distal section (220) fits inside the middle section (230), and the middle section (230) fits inside the proximal section (240). The sections (220, 230, 240) are coupled to each other by any suitable mechanism such that they are capable of sliding in and out.

Thereby, the imaging stylet (200) can be extended from an inactivated compact position shown in FIG. 9B to an activated position shown in FIG. 9A, where the three outer housing sections (220, 230, 240) are extended out of each other such that a maximum length of the outer housing (210) is achieved. Such design of the imaging stylet (200) is advantageous when the stylet is being used in non-operating room conditions, such as, for example, in the field during military operations, where it is necessary to carry compact medical devices.

Although only three outer housing sections are illustrated in FIGS. 9A and 9B, it is understood that the outer housing of the imaging stylet may be comprised of more or fewer than three sections, depending on a particular application.

When a user extends the outer housing (210) from the inactivated position shown in FIG. 9B to the activated position shown in FIG. 9A, a power source coupled to the stylet may be automatically activated to power the device. It is also contemplated that the step of extending the stylet (200) may initiate transmission of image data captured by the imaging device of the stylet to any external device capable of processing and displaying the image data to the user, such as a smartphone, tablet, or a laptop computer.

FIGS. 10A and 10B illustrate an embodiment of the imaging stylet in which the stylet (300) has a folding capability. In this embodiment, the outer housing (310) of the imaging stylet (300) has two separate sections— a distal section (320) with an opening through which the imaging device (340) is extended when in an activated position, and a proximal section (330), to which the control device (350) is coupled for actuation of the imaging device. The two outer housing sections (320, 330) are connected together via a connector (360). Any suitable connector known in the art that allows the two housing sections to be folded and unfolded with respect to teach other may be used in accordance with the present invention.

When in use, the imaging stylet (300) can be quickly and easily unfolded from its inactivated position shown in FIG. 10A to its activated position shown in FIG. 10B, such that a maximum length of the outer housing (310) is achieved. In some advantageous embodiments, unfolding the outer housing (310) from the inactivated position to the activated position activates a power source and initiates transmission of image data from the imaging device (340) to any external processor capable of displaying the image data to the user, such as a smartphone, tablet, laptop computer, etc.

In some advantageous embodiments, such as shown in FIGS. 10A-B, the outer housing (310) of the imaging stylet (300) also includes a coupling device (370) for securing the imaging stylet to an external object, such as a piece of user's clothing. The coupling device (370) may be in a form of a clip or any other suitable device that is capable of removably attaching the imaging stylet to a person's shirt or pant pocket, such that the stylet can be easily carried around and quickly accessible by the user.

It should be understood that the foregoing is illustrative and not limiting, and that obvious modifications may be made by those skilled in the art without departing from the spirit of the invention. Although the invention has been described with reference to embodiments herein, those embodiments do not limit the scope of the invention. Accordingly, reference should be made primarily to the accompanying claims, rather than the foregoing specification, to determine the scope of the invention.

What is claimed is:

1. A method of intubating a patient with a medical intubation device, comprising the steps of:
   deforming a deformable support member to a shape corresponding to a shape of a patient's airway;
   inserting into the patient's airway an imaging stylet deformed to the shape corresponding to the patient's airway, the deformed imaging stylet comprising
      an outer housing having the deformed support member therein such that said outer housing is deformed to the shape corresponding to the shape of the patient's airway by the deformed support member, the outer housing having a proximal end and a distal end with a longitudinal axis, and an opening provided at the distal end;
      an imaging device disposed at the distal end of said outer housing and coupled to the deformable support member; and
      an actuator disposed in said outer housing and coupled to said imaging device;
   moving said imaging device from an inactivated position, in which said imaging device is substantially aligned with the longitudinal axis of said distal end, to an activated position, in which said imaging device extends out of the opening at an angle relative to the longitudinal axis of said distal end, to visualize surrounding tissue in the airway passage; and
   inserting an outer tube into the patient's airway by advancing said outer tube over said outer housing deformed to the shape corresponding to the shape of the patient's airway by the deformed support member.

2. The method according to claim 1, further comprising the step of transmitting image data from said imaging device to a display coupled to said imaging stylet for display to a user.

3. The method according to claim 1, wherein said imaging stylet further comprises a control device positioned at the proximal end of said stylet, and wherein the method further comprises the step of rotationally moving said imaging device via the control device.

4. The method according to claim 1, wherein the outer tube comprises an inflatable balloon positioned adjacent the distal end of the tube, and wherein the method further comprises the step of inflating said balloon by supplying fluid thereto.

5. The method according to claim 1, wherein said imaging stylet further comprises at least one illumination device, and wherein the method further comprises the step of illuminating surrounding tissue via the at least one illumination device.

6. The method according to claim 1, further comprising the step of inserting said support member into said outer housing of said imaging stylet after the step of deforming said support member.

7. The method according to claim 1, wherein the step of deforming said deformable support member comprises deforming said support member while said support member is in said outer housing of said imaging stylet.

8. The method according to claim 1, wherein said imaging stylet further comprises a control device positioned at the proximal end of said imaging stylet, and wherein the method further comprises the step of moving said imaging device from the inactivated position to the activated position via said control device.

9. The method accordingly to claim 8, wherein said control device is removably coupled to said imaging stylet, and wherein the method further comprises the step of removing said control device from said imaging stylet prior to the step of advancing said outer tube over said imaging stylet.

10. The method according to claim 9, wherein:
   said control device comprises a sleeve disposed over the proximal end of said outer housing and movable relative to said outer housing; and
   said actuator comprises a wire connected to said sleeve, such that movement of the sleeve relative to said outer housing causes said actuator to move said imaging device.

11. The method according to claim 10, wherein:
   the proximal end of said outer housing has a wall with an aperture therein; and
   said actuator is connected to said sleeve through said aperture.

12. The method according to claim 11, wherein:
   said aperture is a slit having a first end and a second end;
   said actuator is connected to said sleeve by a stop member extending through said slit; and
   said stop member is movable between the first end of said slit and the second end of said slit to move said imaging device between the inactivated and activated positions.

13. The method according to claim 1, wherein said actuator comprises a nitinol wire.

14. The method according to claim 1, wherein said actuator comprises a stainless steel wire.

15. The method according to claim 1, wherein said outer housing comprises an extruded cylinder having a support lumen for receiving said support member, an actuation lumen for receiving said actuator, and an imaging lumen for receiving said imaging device.

16. The method according to claim 1, wherein said outer housing comprises polyether block amide.

17. The method according to claim 1, wherein said outer housing has an outer diameter of less than about 5 mm.

18. The method according to claim 17, wherein said outer housing comprises an outer diameter of less than 3 mm.

19. The method according to claim 1, wherein said support member comprises a semi-rigid material.

20. The method according to claim 19, wherein said support member comprises aluminum.

21. The method according to claim 1, wherein the angle at which said imaging device extends from the outer shaft is in the range of from about five degrees to about forty degrees.

22. The method according to claim 1, wherein said imaging device comprises a CMOS device.

23. The method according to claim 1, wherein said imaging device comprises a CCD device.

24. The method according to claim 1, wherein said at least one illumination device comprises at least one light emitting diode.

25. The method according to claim 24, wherein said at least one light emitting diode comprises a plurality of light emitting diodes positioned around a lens of said imaging device.

26. The method according to claim 1, further comprising the step of wirelessly transmitting image data from said imaging device to a processor.

27. The method according to claim 1, further comprising the step of transmitting image data from said imaging device to a processor via a cable connection.

28. The method according to claim 1, further comprising the step of storing image data from said imaging device.

29. The method according to claim 1, wherein said outer housing comprises at least two telescoping sections, and wherein the method further comprises the step of extending said outer housing from an inactivated position to an activated position by extending at least one said section out of at least one other said section.

30. The method according to claim 1, wherein said outer housing comprises at least two foldable sections, and wherein the method further comprises the step of moving said outer housing from an inactivated position to an activated position by unfolding the at least two foldable sections.

\* \* \* \* \*